(12) United States Patent
Green et al.

(10) Patent No.: US 8,968,798 B2
(45) Date of Patent: Mar. 3, 2015

(54) COMPOSITIONS OF VOLATILE ORGANIC COMPOUNDS AND METHODS OF USE THEREOF

(71) Applicant: Synthetic Genomics, Inc., La Jolla, CA (US)

(72) Inventors: Wayne A. Green, Encinitas, CA (US); Gary A. Strobel, Bozeman, MT (US)

(73) Assignee: Synthetic Genomics, Inc., La Jolla, CA (US)

( * ) Notice: Subject to any disclaimer, the term of this patent is extended or adjusted under 35 U.S.C. 154(b) by 66 days.

(21) Appl. No.: 13/859,645

(22) Filed: Apr. 9, 2013

(65) Prior Publication Data

US 2013/0224315 A1    Aug. 29, 2013

Related U.S. Application Data

(63) Continuation of application No. 12/753,714, filed on Apr. 2, 2010, now Pat. No. 8,425,946.

(60) Provisional application No. 61/230,672, filed on Jul. 31, 2009, provisional application No. 61/166,694, filed on Apr. 3, 2009.

(51) Int. Cl.
| | |
|---|---|
| *A61K 36/00* | (2006.01) |
| *C12Q 1/02* | (2006.01) |
| *C12N 1/00* | (2006.01) |
| *A01N 65/08* | (2009.01) |
| *A01N 27/00* | (2006.01) |
| *A01N 37/02* | (2006.01) |
| *A01N 37/14* | (2006.01) |
| *A01N 65/00* | (2009.01) |
| *A01C 1/06* | (2006.01) |

(52) U.S. Cl.
CPC ............... *A01N 65/08* (2013.01); *A01N 27/00* (2013.01); *A01N 37/02* (2013.01); *A01N 37/14* (2013.01); *A01N 65/00* (2013.01); *A01C 1/06* (2013.01)
USPC .............................. 424/725; 435/29; 435/243

(58) Field of Classification Search
None
See application file for complete search history.

(56) References Cited

U.S. PATENT DOCUMENTS

| | | | |
|---|---|---|---|
| 3,927,035 | A | 12/1975 | Holmes |
| 4,069,828 | A | 1/1978 | Hall et al. |
| 4,924,000 | A | 5/1990 | Hesse et al. |
| 6,911,338 | B2 | 6/2005 | Strobel et al. |
| 7,070,985 | B2 | 7/2006 | Strobel et al. |
| 7,267,975 | B2 | 9/2007 | Strobel et al. |
| 7,341,862 | B2 | 3/2008 | Strobel et al. |
| 2004/0049059 | A1 | 3/2004 | Mueller |
| 2004/0141955 | A1 | 7/2004 | Strobel et al. |
| 2007/0178128 | A1 | 8/2007 | Bessette |

FOREIGN PATENT DOCUMENTS

| | | |
|---|---|---|
| EP | 1 379 126 B1 | 10/2009 |
| JP | 2002069208 A | 8/2000 |
| WO | WO 02/079476 A1 | 10/2002 |
| WO | WO 2004/034785 A2 | 4/2004 |
| WO | WO 2005/009360 A2 | 2/2005 |

OTHER PUBLICATIONS

Arora et al., "Co-evolution of Pathogens, Mechanism Involved in Pathogenesis and Biocontrol of Plant Diseases: An Overview," In J.M Merillon and K.G. Ramawat (eds.), *Plant Defence: Biological Control* (2012), 3-22, Springer Science+Business Media B.V., Dordrecht, The Netherlands.

Campbell, Richard, "Biological Control of Soil-Borne Diseases: Some Present Problems and Different Approaches," *Crop Protection* (1994), 13(1):4-13, Butterworth-Heinemann Ltd.

Daisy et al., "Naphthalene, an Insect Repellent, is Produced by *Muscodor vitigenus*, a Novel Endophytic Fungus," *Microbiology* (2002), 148:3737-3741.

Ezra et al., "New Endophytic Isolates of *Muscodor albus*, a Volatile-Antibiotic-Producing Fungus," *Microbiology* (2004), 150:4023-4031, The American Society of Biochemistry and Molecular Biology, Inc., U.S.A.

Gosme and Lucas, "Combining Experimentation and Modelling to Estimate Primary and Secondary Infections of Take-All Disease of Wheat," Soil Biol. Biochem. (2009) 41:1523-1530, Elsevier Ltd.

Green et al., "A Record of *Muscodor strobelii*, a Novel Bioactive Endophyte from Malaysia," Accession No. FJ664551, *Muscodor* sp. WG-2009a internal transcribed spacer 1, 5.8S ribosomal RNA gene, and internal transcribed spacer 2, complete sequence, Mar. 3, 2009, Retrieved from Internet: URL: http://lifesciencedb.jp/ddbj/ff_list.cgi?max_num=all&project_id=726826&type=plain.

Kosman, E., "Stochastic Variation and Probabilistic Model—Estimating Frequency of Fungicide Resistant Phenotype in Plant Pathogen Population," *Plant Protect. Sci.* (2002), 38:158-160.

Morris and Kays., "Total Dietary Fiber Variability in a Cross Section of *Crotalaria juncea* Genetic Resources," *Crop Sci.* (2005), 45(5):1826-1829, Crop Science Society of America.

Ning et al., "Research Progress of Drug Resistance Mechanisms of Fungal Pathogens," *Chin. J. Pharmacol. Toxicol.* (2010), 24(5):374-379, Chinese Journal of Pharmacology and Toxicology, Beijing.

(Continued)

*Primary Examiner* — Qiuwen Mi
(74) *Attorney, Agent, or Firm* — DLA Piper LLP (US)

(57) ABSTRACT

The present invention provides compositions and methods for treating, inhibiting or preventing the developing of a plant pathogenic disease. The compositions comprise volatile organic compounds effective to inhibit the growth of, or kill pathogenic microbes, including *Ganoderma boninense*. Invention compositions are especially useful in preventing and treating basal stem rot in the oil palm, and can be applied in the vicinity of the plant or used to sterilize the plant growth medium prior to or concurrent with plant growth therein.

22 Claims, 1 Drawing Sheet

(56) References Cited

OTHER PUBLICATIONS

Plant Pathology from Wikipedia, accessed on Aug. 21, 2012, pp. 1-8.
Prithiviraj and Singh, "Risk Potential of a Biocontrol Agent Unmasked," *Curr. Sci.* (1997), 73(8):643-644.
Strobel et al., "Volatile Antimicrobials from *Muscodor albus*, a Novel Endophytic Fungus," *Microbiology* (2001), 147:2943-2950, SGM, Great Britain.
Strobel et al., "*Muscodor albus* E-6, an Endophyte of *Guazuma ulmifolia* Making Volatile Antibiotics: Isolation, Characterization and Experimental Establishment in the Host Plant," *Microbiology* (2007), 153:2613-2620, SGM, Great Britain.

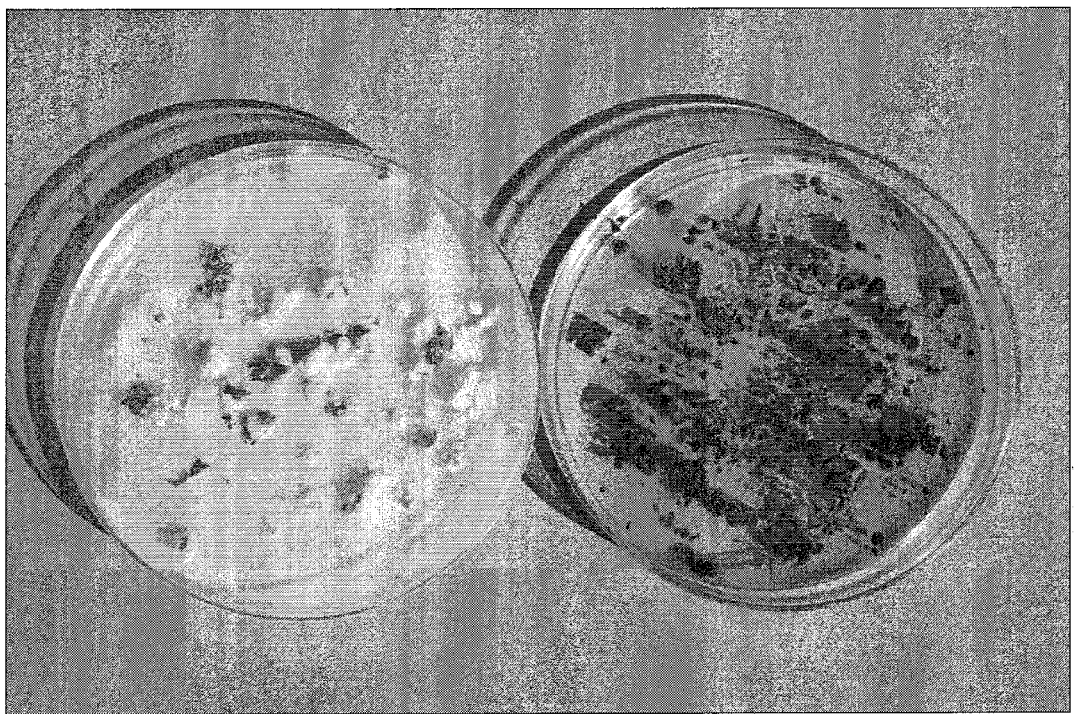

COMPOSITIONS OF VOLATILE ORGANIC COMPOUNDS AND METHODS OF USE THEREOF

CROSS-REFERENCE TO RELATED APPLICATIONS

This application is a continuation application of U.S. application Ser. No. 12/753,714 filed Apr. 2, 2010, now issued as U.S. Pat. No. 8,425,946; which claims the benefit under 35 U.S.C. §119(e) to U.S. Application Ser. No. 61/230,672 filed Jul. 31, 2009 and to U.S. Application Ser. No. 61/166,684 filed on Apr. 3, 2009. The disclosure of each of the prior applications is considered part of and is incorporated by reference in the disclosure of this application including all tables, figures and claims.

BACKGROUND OF THE INVENTION

1. Field of the Invention

The present invention relates to compositions of volatile organic compounds with biological activity against plant pathogens, particularly the fungus *Ganoderma boninense* that is a causative agent of the oil palm disease *Ganoderma* Basal Stem Rot. The disclosure also provides compositions comprising at least one known pesticidal agent useful for selective pest control applications.

2. Background Information

Oil palm, *Elaeis guineensis*, is the most important plantation crop in Malaysia. Four tons of palm oil are produced annually per hectare from this crop plant. Many small private landowners are able to profit from the production and sale of the palm oil, making this an activity of great economic importance. Presently, Malaysia's oil palm industry is under threat as it is faced with a very serious plant disease problem. This problem is a prevailing incurable oil palm disease called *Ganoderma* Basal Stem Rot (BSR) caused by *Ganoderma boninense*. Presently, BSR is rapidly becoming the major threat to oil palm cultivation and palm oil production in Southeast Asia.

In BSR disease, basal stem rot is only one part of the disease cycle. *Ganoderma boninense* also causes a seedling disease and an upper stem rot of more developed palms. Spores of *G. boninense* have multiple roles in the infection process to bring about the three distinct phases of this important plant disease. This pathogenic organism is also prevalent on other major plantation plants including coconut, betel nut, tea, cacao, acacia and poplar.

With no effective cure at present, BSR has a huge economic impact on the Malaysian oil palm industry. Thus, plant health is crucial in obtaining maximal productivity of the oil palm and techniques, methods and management ideas are needed to control BSR. Attempts to control this disease with agrochemicals have not been very successful. This could be due to the fact that the oil palms already possessed latent fungal infections at the time of the chemical treatment. Biological control agents have also been tried against *Ganoderma* with limited success. Saprophytic organisms (such as *Trichoderma harzianum*) merely arrest the spread of disease by competing against *Ganoderma* to reduce its opportunity to colonize oil palm roots.

BSR is a particular concern because the activity of replanting oil palms can accelerate spread of the disease. It is well known that successive replanting of oil palms can be rapidly exploited by soil borne fungi such as *Ganoderma*. Soils that continuously support the growth of palms eventually act as a reservoir for *Ganoderma* fruiting structures and spores of this organism. Soils that are replanted with new palms are immediately exposed to a high load of inoculum (spores) and eventually become infected by *Ganoderma boninense*.

It is widely believed that the problem of basal stem rot of palm will become increasingly serious as more and more established plantations become due for second or even third replanting. Environmental considerations, coupled with governmental directives, will reduce exploitation of new forest areas, making further replanting of these crops necessary. There is a need for integrated management systems for *Ganoderma* and related diseases to maintain the success of the oil palm industry.

SUMMARY OF THE INVENTION

The compositions of the present invention may be used to control major diseases of plants caused by a variety of plant pathogens. One exemplary plant is the oil palm, whereby compounds may inhibit or prevent the development of basal stem rot disease. These compounds may target *Ganoderma boninense*, a causative agent of basal stem rot disease.

One aspect of the invention provides a composition for treating, inhibiting or preventing at least one plant pathogenic disease. The composition comprises two or more compounds wherein at least one of the compounds is isobutyric acid, methyl isobutyrate or isobutyric anhydride. The second compound of the composition is selected from isobutyric acid, methyl isobutyrate, isobutyric anhydride, ethyl isobutyrate, propyl isobutyrate, isobutyric acid-allyl ester, naphthalene, caryophyllene, and a plant essential oil. The composition may also be a combination of three or more of these compounds, or may further include additional components, including volatile organic compounds (VOCs). Additional compounds may include, but are not limited to, one or more of naphthalene or naphthalene derivatives, caryophyllene, isocaryophyllene, α-humulene, and the compounds provided in Table 1 herein; compounds produced by *Muscodor* species, such as the volatile organic compounds listed in Table 2 herein; and plant essential oils, such as those listed in Table 3 herein.

In some preferred embodiments, the composition includes 20-70% isobutyric acid, 20-70% methyl isobutyrate, 20-70% isobutyric anhydride, or any combination thereof. In further embodiments, this composition further comprises 1-10% naphthalene, caryophyllene, or a plant essential oil. In certain preferred embodiments, the composition comprises 42-53% isobutyric acid, 42-53% methyl isobutyrate, and 3-7% naphthalene, caryophyllene, or a plant essential oil. In other preferred embodiments, the composition includes 42-53% isobutyric acid, 42-53% isobutyric anhydride, and 3-7% naphthalene, caryophyllene, or a plant essential oil.

In other preferred embodiments, the composition further comprises an agriculturally effective amount of a pesticidal compound or composition. The additional compound or composition may be an acaricide, a bactericide, a fungicide, an insecticide, a microbicide, a nematicide, or a food preservative.

The composition in some embodiments may be in the form of a powder, a granule, a pellet, a gel, an aqueous suspension, a solution or an emulsion. The composition may be provided with a carrier, such as an agriculturally acceptable carrier. The carrier can be a seed.

Another aspect of the invention provides a method for treating, inhibiting or preventing the development of a plant pathogenic disease, comprising applying a composition of the invention in the vicinity of the plant. In a preferred embodiment, the pathogen may be *Aspergillus fumigatus, Botrytis cinerea, Cerpospora betae, Curvularia* sp., *Gano-*

*derma boninense, Geotrichum candidum, Mycosphaerella fijiensis, Phytophthora palmivora, Phytophthora ramorum, Pythium ultimum, Rhizoctonia solani, Rhizopus* sp., *Schizophyllum* sp., *Sclerotinia sclerotiorum, Verticillium dahliae*, or *Xanthomonas axonopodis*. In another preferred embodiment, the host plant is susceptible to disease caused by *Ganoderma boninense*. In another preferred embodiment, the host plant is an oil palm plant. In certain embodiments, the method is effective to inhibit the growth of the plant pathogen. In preferred embodiments, the method is effective to kill the plant pathogen.

Some embodiments provide for the composition to be applied to the vicinity or a plant, such as around the roots, stems, trunk, seed, or leaves of the plant, applied onto such parts of the plant, or injected into such parts of the plant. In other embodiments, the composition can be used to treat or sterilize the soil or plant growth medium, by exposing the soil or plant growth medium to vapors from the invention composition, or by direct contact, such as intermixing, with the composition.

Another aspect of the invention provides a method for screening microbial strains that may be useful for treating, inhibiting or preventing the development of a plant pathogenic disease. The method comprises (i) exposing or contacting candidate microbial strains with an invention composition, (ii) selecting microbial strains resistant to the composition, and (iii) characterizing the selected microbial strain. The invention also includes the microbial strains obtained from the method as described above.

Another aspect of the invention relates to a method for killing, inhibiting or preventing the development of an undesired organism, such as a fungus, a bacterium, a microorganism, a nematode, and an insect. The method comprises exposing or contacting the organism to or with an effective amount of an invention composition.

These and other objects and features of the invention will become more fully apparent when the following detailed description of the invention is read in conjunction with the accompanying drawing.

BRIEF DESCRIPTION OF THE DRAWINGS

FIG. 1 depicts the effect of treating soil with a composition of the invention. Treated soil on the right shows no growth of microorganisms on soil inoculated with *Ganoderma boninense*; while the untreated control plate on the left shows extensive growth.

DETAILED DESCRIPTION OF THE INVENTION

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference; and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof.

Bactericidal: The term "bactericidal", as used herein, refers to the ability of a substance to increase mortality or inhibit the growth rate of bacteria.

Biological Control: As used herein, "biological control" is defined as control of a pathogen or insect or any other undesirable organism by the use of a second organism. An example of a known mechanism of biological control is the use of enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

Culturing: The term "culturing", as used herein, refers to the propagation of organisms on or in media of various kinds.

Composition: A "composition" is intended to mean a combination of active agent and another compound, carrier or composition, inert (for example, a detectable agent or label or liquid carrier) or active, such as a pesticide.

Derivative: As used herein, a "derivative" of a chemical compound is a compound that can be chemically or biologically derived from the original compound, for example by the addition, substitution or deletion of chemical components of the original compound. For example, a derivative may be an isomer of the referenced compound, an anhydride of the referenced compound, or has one or more chemical groups added or substituted with respect to the referenced compound. For example, propanoic acid, 2-methyl, 3-methylbutyl ester is considered to be a derivative of propanoic acid.

Effective Amount: An "effective amount", as used herein, is an amount sufficient to affect beneficial or desired results. An effective amount can be administered in one or more administrations. In terms of treatment, inhibition or protection, an effective amount is that amount sufficient to ameliorate, stabilize, reverse, slow or delay progression of the target infection or disease states.

Fungicidal: As used herein, "fungicidal" refers to the ability of a substance to decrease the rate of growth of fungi or to increase the mortality of fungi.

Fungus: The term "fungus" or "fungi", as used herein, includes a wide variety of nucleated spore-bearing organisms that are devoid of chlorophyll. Examples of fungi include yeasts, molds, mildews, rusts, and mushrooms.

Insecticidal: As used herein, 'Insecticidal' refers to the ability of a substance to increase mortality or inhibit the growth rate of insects or their larvae.

Microbicidal: "Microbicidal", as used herein, refers to the ability of a substance to increase mortality or inhibit the growth rate of microorganism.

Mutant: As used herein, the term "mutant" or "variant" refers to a modification of the parental strain in which the desired biological activity remains similar to that of the parental strain. Mutants or variants may occur in nature without the intervention of man. They also are obtainable by treatment with or by a variety of methods and compositions known to those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means well known to those practiced in the art.

Nematicidal: The term "nematicidal", as used herein, refers to the ability of a substance to increase mortality or inhibit the growth rate of nematodes.

Plant Oil: A "plant oil", "plant essential oil", or "plant volatile oil", as used herein, is any oil derived from any part of a plant, and includes any compound purified or derived from a plant oil, such as a hydrophobic, volatile organic compound that is produced by a plant species. An exemplary plant essential oil is caryophyllene, a natural bicyclic sesquiterpene that is a constituent of many plant essential oils, such as oils obtained from cannabis (*Cannabis sativa*), hemp, marijuana, caraway (*Carum carvi*), cloves (*Syzygium aromaticum*), hops (*Humulus lupulus*), basil (*Ocimum*), oregano (*Origanum vulgare*), pepper (*Piper nigrum*), rosemary (*Rosmarinus oficinalis*), cinnamon (*Cimmamomun zeylanicum* or *tamala*). A plant essential oil used in a composition as disclosed herein need not be isolated from a plant, for example, it may be chemically synthesized or isolated from a microorganism that produces the compound. Exemplary plant essential oils are provided in Table 3 herein.

Pesticidal: The term "pesticidal", as used herein, refers to the ability of a substance to decrease the rate of growth of a pest, i.e., an undersired organism, or to increase the mortality of a pest.

Volatile: "Volatile compounds" and "volatile organic compounds" (VOCs), as used herein, are compounds that in most instances evaporate readily at ambient temperature and pressure. Volatile compounds of the present invention must be present "in the vicinity" of the target pathogen organism for effectiveness. The invention compositions are thus placed in the vicinity of the host plant or the target organism, or in the growth medium or soil of the host plant prior to or concurrent with plant growth. Generally, volatile compounds are in the vicinity of the target pathogenic organism so long as they achieve their biological effect prior to evaporation. They may be spread on or around the base of the host plant or intermixed with the growth medium or soil of the plant. Physical contact with the host plant or target pathogen is not required due to the dispersal of the volatiles through the air or soil.

The discussion of the general methods given herein is intended for illustrative purposes only. Other alternative methods and embodiments will be apparent to those of skill in the art upon review of this disclosure.

Compositions of Volatile Organic Compounds

The invention provides compositions of volatile organic compounds that can be used to treat or prevent growth of a pathogen, such as but not limited to a plant pathogen. Table 1 provides exemplary compounds that can be used in compositions and methods of the present invention. Table 2 herein provides the VOCs produced by a fourteen day old culture of *Muscodor strobelii*. *M. strobelii* producing these compounds was demonstrated to be lethal to several species of pathogenic microorganisms including *Aspergillus fumigatus, Botrytis cinerea, Cerpospora betae, Curvularia* sp., *Ganoderma boninense, Geotrichum candidum, Mycosphaerella fijiensis, Phytophthora palmivora, Phytophthora ramorum, Pythium ultimum, Rhizoctonia solani, Rhizopus* sp., *Schizophyllum* sp., *Sclerotinia sclerotiorum, Verticillium dahliae*, and *Xanthomonas axonopodis*.

TABLE 1

Compounds of the Present Invention

| Compound | IUPAC Name | CAS Registry # | MW |
| --- | --- | --- | --- |
| ethanol | ethanol | 64-17-5 | 46 |
| acetone | propanone | 67-64-1 | 58 |
| 2-butanone | butan-2-one | 78-93-3 | 72 |
| methyl acetate | methyl acetate | 79-20-9 | 74 |
| isobutyl alcohol | 2-methylpropan-1-ol | 78-83-1 | 74 |
| isobutyric acid | 2-methyl propanoic acid | 79-31-2 | 88 |
| ethyl acetate | ethyl acetate | 141-78-6 | 88 |
| N,2-dimethylpropanamide | | 2675-88-9 | 101 |
| isobutyric acid, methyl ester (methyl isobutyrate) | methyl-2-methylpropanoate | 547-63-7 | 102 |
| 1-(ethenyloxy)-3-methyl-butane | | 39782-38-2 | 114 |
| octane | octane | 111-65-9 | 114 |
| methyl 2-methoxypropenoate | | 17639-76-8 | 116 |
| butyl acetate | butyl ethanoate | 123-86-4 | 116 |
| isobutyl acetate | isobutyl acetate | 110-19-0 | 116 |
| isobutyric acid, ethyl ester (ethyl isobutyrate) | ethyl-2-methylpropanoate | 97-62-1 | 116 |
| phenethyl alcohol | 2-phenylethanol | 60-12-8 | 122 |
| allyl 2-methylpropanoate | | 15727-77-2 | 128 |
| naphthalene | naphthalene | 91-20-3 | 128 |
| methyl 2,3-dimethylbutanoate | | 30540-29-5 | 130 |
| isobutyric acid, propyl ester (propyl isobutyrate) | propyl-2 methylpropanoate | 644-49-5 | 130 |
| 3-methyl-1-butanol | 3-methyl-1-butanol | 123-51-3 | 131 |
| 2-nonanone | heptyl methyl ketone | 821-55-6 | 142 |
| 2-methylheptanoic acid | | 1188-02-9 | 144 |
| acetic acid, (tert-butylthio)- | | 24310-22-3 | 148 |
| pentamethyl-benzene | | 700-12-9 | 148 |
| 2-(1-Propenyl)-6-methylphenol | | | 148 |
| undecane | undecane | 1120-21-4 | 156 |
| isobutyric anhydride | 2-methylpropanoyl 2-methyl propanoate | 97-72-3 | 158 |
| 4,4-diethyl-2,5-octadiyne | | 61227-87-0 | 162 |
| butyl propyl oxalate | | 26404-30-8 | 188 |
| 4,5-dimethyl-1,2,3,6,7,8,8a,8b-octahydrobiphenylene | | | 188 |
| 4,5-dehydro-isolongifolene | | | 202 |
| alpha-gurjunene | | 489-40-7 | 204 |
| (−)-arstolene | | 25274-27-5 | 204 |
| alpha-patchoulene | | 560-32-7 | 204 |
| (−)-tricyclo[6.2.1.0(4,11)]undec-5-ene,1,5,9,9-tetramethyl-(isocaryophyllene-II) | | | 204 |
| bergamotene | | 6895-56-3 | 204 |

TABLE 1-continued

Compounds of the Present Invention

| Compound | IUPAC Name | CAS Registry # | MW |
|---|---|---|---|
| (Z)-7,11-dimethyl-3-methylene-1,6,10-dodecatriene | | | 204 |
| caryophyllene | 4,11,11-trimethyl-8-methylene-bicyclo[7.2.0]undec-4-ene | 87-44-5 | 204 |
| heptyl allyl oxalate | | | 228 |
| isoamyl isobutyrate | 3-methylbutyl 2-methylpropanoate | 2050-01-3 | 316 |

In some embodiments of the invention, a composition used to inhibit or prevent development of a plant pathogenic disease, or infestation by a plant pathogen comprises at least 20 percent, at least 25 percent, at least 30 percent, at least 35 percent, at least 40 percent, at least 45 percent, at least 50 percent, at least 55 percent, at least 60 percent, at least 65 percent or at least 70 percent isobutyric acid, methyl isobutyrate or isobutyric anhydride. A preferred range is 20-70%, 30-60%, or 40-50%, and a most preferred range is 42-53%.

In some embodiments, a composition of the invention further includes, as a second compound, at least 20 percent, at least 25 percent, at least 30 percent, at least 35 percent, at least 40 percent, at least 45 percent, at least 50 percent, at least 55 percent, at least 60 percent, at least 65 percent, or at least 70 percent isobutyric acid, methyl isobutyrate, isobutyric anhydride, ethyl isobutyrate, propyl isobutyrate, isobutyric acid-allyl ester. A preferred range is 20-70%, 30-60%, or 40-50%, and a most preferred range is 42-53%.

In some embodiments, a composition of the invention further includes, as a second or third compound, at least 1 percent, at least 2 percent, at least 3 percent, at least 4 percent, at least 5 percent, at least 6 percent, at least 7 percent, at least 8 percent, at least 9 percent or at least 10 percent of naphthalene, caryophyllene or a plant essential oil. A preferred range is 1-10%, 2-9%, or 3-8%, and a most preferred range is 3-7%.

A composition of the invention can include one or more additional compounds, which can be any compounds that do not negatively affect the ability of the composition to inhibit the growth of or kill one or more pathogenic microorganisms, where a pathogenic microorganism can be a microorganism that causes disease in a plant or an animal. In some examples, a composition of the invention includes one or more VOCs in addition to isobutyric acid, methyl isobutyrate, or isobutyric anhydride. For example, the composition can include additional VOCs produced by *M. strobelii* or other fungi, including other *Muscodor* species. A composition may also be a combination of three or more of these compounds, or may further include additional components, including volatile organic compounds (VOCs) and plant essential oils. Additional compounds may include, but are not limited to, one or more of naphthalene or naphthalene derivatives, caryophyllene, isocaryophyllene, α-humulene, and the compounds provided in Table 1 herein; compounds produced by *Muscodor* species, such as the volatile organic compounds listed in Table 2 herein; and plant essential oils, such as those listed in Table 3 herein.

For example, *Muscodor albus* produces, among other VOCs, octane, acetone, ethanol, isobutyl alcohol, methyl acetate, ethyl acetate, various methyl esters of propanoic acid, butanol derivatives, furan, nonanone derivatives, naphthalene, azulene, cyclohexene and caryophyllene (U.S. Pat. No. 6,911,338, incorporated herein by reference). *Muscodor vitigenus* produces, for example, naphthalene and naphthalene derivatives, among other VOCs (U.S. Pat. No. 7,267,975, incorporated herein by reference). VOCs identified as produced by *M. strobelii* are provided herein in Table 2. Volatile compounds produced by *M. albus, M. vitigenus,* or *M. strobelii* can be used in a composition of the invention, in addition to derivatives of these compounds.

Other compounds that can be included in a composition of the invention include plant essential oils. Plant essential oils can include volatile hydrocarbon compounds obtained from any part of a plant, including the leaves, stems, roots, seeds, bark, wood, fruit (including rinds), or flowers of plant, or any oil derived from any plant parts. Included without limitation are oils extracted or derived from *Mentha arvensis, Eucalyptus, Lisea cubea,* peppermint, spearmint, wintergreen, clove, lemon, grapefruit, lime, tangerine, and orange, as well as oils extracted or derived from allspice or juniper berries, from anise, celery, or cumin seeds, or from almonds or nutmeg, and any constituents or derivatives thereof. Also included are oils extracted or derived from basil, bay, cinnamon, sage, lemon grass, *Melaleuca,* oregano, rosemary, patchouli, pine, cannabis, chamomile, sage, clove, geranium, hops, hyssop, jasmine, lavender, manuka, marjoram, camphor, rosewood, cedarwood, sandalwood, agarwood, ginger, galangal, tea tree, bergamot, and valerian, and any constituents or derivatives thereof. Table 3 provides some examples of plant essential oils that can be used in compositions of the invention.

An exemplary composition of the invention is a mixture of isobutyric acid, methyl isobutyrate, and naphthalene. For example, compositions may comprise 20-70% isobutyric acid, 20-70% methyl isobutyrate, and 1-10% naphthalene. In some embodiments, the composition comprises 30-60% isobutyric acid. In some embodiments, the composition comprises 30-60% methyl isobutyrate. In some embodiments, the composition comprises 42-53% isobutyric acid, 42-53% methyl isobutyrate, and 3-7% naphthalene. For example, the composition can comprises 47.5% isobutyric acid, 47.5% methyl isobutyrate, and 5% naphthalene.

Another exemplary composition is a mixture of isobutyric acid, isobutyric anhydride, and naphthalene. For example, compositions may comprise 20-70% isobutyric acid, 20-70% isobutyric anhydride, and 1-10% naphthalene. In some embodiments, the composition comprises 30-60% isobutyric acid. In some embodiments, the composition comprises 30-60% isobutyric anhydride. In some embodiments, the composition comprises 42-53% isobutyric acid, 42-53% isobutyric anhydride, and 3-7% naphthalene. For example, the composition can comprise 47.5% isobutyric acid, 47.5% isobutyric anhydride, and 5% naphthalene.

Other examples of compositions of the invention include mixtures of isobutyric acid, an isobutyric acid derivative, and one or more plant essential oil, which can be any plant essential oil, including but not limited to plant essential oils as provided in Table 3. In some embodiments, a plant essential oil used in a composition of the invention is caryophyllene or a derivative of caryophyllene, such as isocaryophyllene or α-humulene. For example, in some embodiments, a composition includes 20-70% isobutyric acid, 20-70% methyl isobutyrate or isobutyric anhydride, and 1-10% of a plant essential oil.

One exemplary composition is a mixture of isobutyric acid, methyl isobutyrate, and caryophyllene. For example, compositions may comprise 20-70% isobutyric acid, 20-70% methyl isobutyrate, and 1-10% caryophyllene. In some embodiments, the composition comprises 30-60% isobutyric acid. In some embodiments, the composition comprises 30-60% methyl isobutyrate. In some embodiments, the composition comprises 42-53% isobutyric acid, 42-53% methyl isobutyrate, and 3-7% caryophyllene. For example, the composition can comprises 47.5% isobutyric acid, 47.5% methyl isobutyrate, and 5% caryophyllene.

Yet another exemplary composition is a mixture of isobutyric acid, isobutyric anhydride, and caryophyllene. For example, compositions may comprise 20-70% isobutyric acid, 20-70% isobutyric anhydride, and 1-10% caryophyllene. In some embodiments, the composition comprises 30-60% isobutyric acid. In some embodiments, the composition comprises 30-60% isobutyric anhydride. In some embodiments, the composition comprises 42-53% isobutyric acid, 42-53% isobutyric anhydride, and 3-7% caryophyllene. For example, the composition can comprise 47.5% isobutyric acid, 47.5% isobutyric anhydride, and 5% caryophyllene.

In yet other embodiments, the composition can include, in addition to isobutyric acid and, optionally a derivative thereof, one or more sesquiterpenes, such as the sesquiterpenes present in the VOCs of *M. strobelii*. A sesquiterpene used in a composition of the invention can be a pheromone, such as a pheromone that affects the behavior of one or more insect species. For example, sesquiterpene compounds such as iso-caryophyllene or derivatives thereof (e.g., (−)-tricyclo [6.2.1.0(4,11)]undec-5-ene,1,5,9,9-tetramethyl-(isocaryophyllene-II), bergamotene or derivatives thereof, patchoulene or derivatives thereof (e.g., alpha-patchoulene), gurjunene or derivatives thereof (e.g., alpha-gurjunene), aristolene or derivatives thereof (e.g., (−)-aristolene, or isolongifolene or derivatives thereof (e.g., 4,5-dehydro-isolongifolene) present individually at molar percentages of 10 percent or less in the mixture of VOC s produced by a *Muscodor* strain can be present in a composition of the invention.

The disclosure provides compositions of compounds and optionally a carrier. The carrier may be any one or more of a number of carriers that confer a variety of properties, such as increased stability, wettability, dispersability, etc. Suitable formulations that may be prepared include wettable powders, granules, pellets, gels, microencapsulated particles, and the like, liquids such as aqueous flowables, aqueous suspensions, etc. The carrier may be an agricultural carrier. In certain embodiments the carrier is a seed, and the composition may be applied or coated onto the seed or allowed to saturate the seed.

The agricultural carrier may be soil or plant growth medium. Other agricultural carriers that may be used include water, fertilizers, plant-based oils, humectants, or combinations thereof. The composition can be provided as a solution that is injected or intermixed into the soil. The composition can be formulated as a particle or granule having a coating that dissolves over time or on wetting to release the volatile composition.

Alternatively, the agricultural carrier may be a solid, such as diatomaceous earth, alginate, clay, other plant and animal products, or combinations, including granules or suspensions. For example, the aqueous suspension, solution, or emulsion may be provided with a carrier to facilitate dispersal of the composition through the soil. Materials such as vermiculite, peat, natural or man-made fibers, or biological material such as seed, plant parts, empty fruit bunches (EFBs) from palm, sugar cane bagasse, hulls or stalks from grain processing, ground plant material ("yard waste") or wood from building site refuse, sawdust or small fibers from recycling of paper, fabric, or wood can be soaked in the composition, and then mixed with the soil or growth medium used for planting a plant species of interest. The agricultural carrier, soil or plant growth medium need not be in direct contact with the composition, for example, it can be treated or sterilized by vapors from the composition in the vicinity.

When used as pesticides or fungicide in their commercially available formulations and in the use forms prepared with these formulations, the active compounds according to the invention can furthermore be present in the form of a mixture with synergists. Synergists are compounds by which the activity of the active compounds is increased without it being necessary for the synergist added to be active itself.

When used as pesticides in their commercially available formulations and in the use forms prepared with these formulations, the active compounds according to the invention can furthermore be present in the form of a mixture with inhibitors which reduce the degradation of the active compound after application in the habitat of the plant, on the surface of parts of plants or in plant tissues.

The active compounds according to the invention, as such or in their formulations, can also be used as a mixture with known acaricides, bactericides, fungicides, insecticides, microbicides, or nematicides, or combinations thereof, for example in order to widen the spectrum of action or to prevent the development of resistances in this way. In many cases, synergistic effects result, i.e. the activity of the mixture can exceed the activity of the individual components. A mixture with other known active compounds, such as fertilizers, growth regulators, safeners and/or semiochemicals is also possible.

In a preferred embodiment of the present invention, the composition may include at least one of a biological and an additional chemical pesticide. Exemplary chemical pesticides include those in the organophosphate, carbamate, organochlorine, and prethroid classes. Also included are chemical control agents such as, but not limited to, benomyl, borax, captafol, captan, chorothalonil, formulations containing copper; formulations containing zinc; dichlone; dicloran; iodine; fungicides that inhibit ergosterol biosynthesis such as but not limited to fenarimol, imazalil, myclobutanil, propiconazole, prochloraz, terbutrazole, flusilazole, triadimefon, and tebuconazole; folpet ipordione; manocozeb; maneb; metalaxyl; oxycarboxin, oxytetracycline; PCNB; pentachlorophenol; quinomethionate; sodium aresenite; sodium DNOC; sodium hypochlorite; sodium phenylphenate; streptomycin; sulfur; thiabendazolel; thiophanate-methyl; triforine; vinclozolin; zineb; ziram; tricyclazole; cymoxanil; blastididin; and validimycin.

Exemplary biological pesticides include microbes, animals, plants, bacteria, genetic material, and natural products of living organisms. For example, fungi that can be combined with a composition that includes isobutyric acid, methyl isobutyrate, or isobutyric anhydride, include, without limitation, *Muscodor* species, *Fusarium lateritium, Metarhizium anisopliae* ("green muscarine"), *Metarhizium flaviride, Beauveria bassiana* ("white muscarine"), *Beauveria brongniartii, Chladosporium herbarum, Paecilomyces farinosus, Paecilomyces fitmosoroseus, Verticillium lecanii, Hirsutella citriformis, Hirsutella thompsoni, Aschersonia aleyrodis, Entomophaga grylli, Entomophaga maimaiga, Entomophaga muscae, Entomophaga praxibulli, Entomophthora plutellae, Zoophthora radicans, Neozygitesfloridana, Nomuraea rileyi, Pandora neoaphidis, Tolypocladium cylindrosporum, Culicinomyces clavosporus, Muscodor albus, Cordyceps variabilis, Cordyceps facis, Cordyceps subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis and Cordyceps clavulata, and mycorrhizal species such as Laccaria bicolor. Other mycopesticidal species will be apparent to those skilled in the art.

Exemplary food preservatives include antimicrobial preservatives, which inhibit the growth of bacteria and fungi and mold growth, or antioxidants such as oxygen absorbers, which inhibit the oxidation of food constituents. Common antimicrobial preservatives include calcium propionate, sodium nitrate, sodium nitrite, sulfites (sulfur dioxide, sodium bisulfite, potassium hydrogen sulfite, etc.) and disodium EDTA. Antioxidants include BHA and BHT. Other preservatives include formaldehyde (usually in solution), glutaraldehyde (kills insects), ethanol and methylchloroisothiazolinone.

Using methods well known to those of skill in the art, the volatile organic compounds may also be used to treating or protecting non-plant materials from fungal or toxic mold infestations. For example, the volatile compounds may be used to treat or prevent toxic mold on building materials and in buildings by contacting the building, the building materials, or the spaces between the building materials with an effective amount of the volatile composition. Further, an effective amount of the volatile compounds can be used alone or in combination with other fumigants in a room or alternatively, during whole building fumigations.

Treating Plant Pathogens Volatile Organic Compounds

The invention further provides a method for treating, inhibiting, or preventing the development of a plant pathogen disease comprising applying a composition of the invention to a plant, or in the vicinity of the plant prior to or concurrent with plant growth. The plant treated according to the methods of the invention can be any type of plant, including trees, crop plants, and ornamental plants of any species. Where the composition is applied to the soil or a growth medium, the soil or medium can support the growth of any type of plant. For example, a composition of the invention can be applied to an oil palm (Elaeis guineensis), coconut (Cocos nucifera), betel (Areca catechu), tea (Camellia sinensis), cocoa (Theobroma cacao), acacia (Acacia species), or poplar (Populus species) plant, or soil or a growth medium that supports growth of any of these or other plant species.

The composition can be any disclosed herein. In some preferred embodiments, the composition comprises isobutyric acid, methyl isobutyrate, and naphthalene. In some embodiments, the composition comprises 20-70% isobutyric acid, 20-70% methylisobutyrate, and 1-10% naphthalene. In some exemplary embodiments, the composition comprises 42-53% isobutyric acid, 42-53% methylisobutyrate, and 3-7% naphthalene.

In other preferred embodiments, the composition comprises isobutyric acid, isobutyric anhydride, and caryophyllene. In some embodiments, the composition comprises 20-70% isobutyric acid, 20-70% isobutyric anhydride, and 1-10% caryophyllene. In some exemplary embodiments, the composition comprises 42-53% isobutyric acid, 42-53% isobutyric anhydride, and 3-7% caryophyllene.

The composition can include carriers or other compounds that aid in application of the compounds to the plant, and/or adherence of the compound to the plant or vicinity of the plant. For example, the composition can be in the form of an emulsion, such as a water-in-oil emulsion, or can be provided with one or more surfactants, such as an ionic or nonionic surfactant. The composition of volatile organic compounds can be provided with a carrier such as particles or powder. Other exemplary carriers include soil, the agricultural and absorbent carriers listed below, and seeds, branches, mulch, and plant fragments that can be spread at the base of the plant. Carriers also include compounds known to those of skill in the art that reduce the volatility of the volatile organic compounds during storage, shipment, and plant treatment. Such carriers may be desirable to affect a controlled release of the volatile organic compounds during plant treatment.

In some embodiments, the composition is a liquid composition, and may be an emulsion, and the composition is used to wipe, water, spray, or drench the plant or areas of the plant, such as the roots. Plants, or parts of plants such as the roots, can in some embodiments be dunked into the composition or wrapped in a fabric, fibers, or a filter or matrix that contains or is saturated with the composition prior to planting or transplanting. In some embodiments, the composition is injected into a plant, for example, into the roots, trunk, stems, or leaves. In some embodiments, the volatile organic compound composition is watered into the soil.

A seed coating or seed dressing formulation can be applied to the seeds employing the compositions of the invention and a diluent in suitable seed coating formulation form, e.g., as an aqueous suspension or in a dry powder form having good adherence to the seeds. Such seed coating or seed dressing formulations are known in the art. Such formulations may contain the single active ingredients or the combination of active ingredients in encapsulated form, e.g., as slow release capsules or microcapsules.

The composition may be topically administered to plants, including any or all plant parts, including without limitation, roots, shoots, stems, bark, leaves, fruit, and/or seeds. For example, the volatile compound composition may be applied on, in, or near the root of the oil palm. Single and multiple applications are contemplated. Multiple applications can be through more than one application method.

The compositions of the invention are particularly useful in combating plant pests and plant pathogens, particularly phytopathogenic fungi. Thus, the invention has may be used to treat, inhibit or prevent the development of plant pathogenic diseases caused by a broad range of fungi. The compositions and methods of the present invention are preferably used against fungi that are important or interesting for agriculture, horticulture, plant biomass for the production of biofuel molecules and other chemicals, and/or forestry. Non-limiting examples include, for instance, Acremonium strictum, Agrobacterium tumefaciens, Alternaria alternata, Alternaria solani, Aphanomyces euteiches, Aspergillus fumigatus, Athelia rolfsii, Aureobasidium pullulans, Bipolaris zeicola, Botrytis cinerea, Calonectria kyotensis, Cephalosporium maydis, Cercospora medicaginis, Cercospora sojina, Colletotrichum coccodes, Colletotrichum fragariae, Colletotrichum graminicola, Coniella diplodiella, Coprinopsis psychromorbida, Corynespora cassiicola, Curvularia pallescens, Cylindrocladium crotalariae, Diplocarpon earlianum, Diplodia gossyina, Diplodia spp., Epicoccum nigrum, Erysiphe cichoracearum, Fusarium graminearum, Fusarium oxysporum, Fusarium oxysporum f.sp. tuberosi, Fusarium proliferatum var. proliferatum, Fusarium solani, Fusarium verticillioides, Ganoderma boninense, Geotrichum candidum, Glomerella tucumanensis, Guignardia bidwellii, Kabatiella zeae, Leptosphaerulina briosiana, Lep-

*totrochila medicaginis, Macrophomina, Macrophomina phaseolina, Magnaporthe grisea, Magnaporthe oryzae, Microsphaera manshurica, Monilinia fructicola, Mycosphaerella fijiensis, Mycosphaerella fragariae, Nigrospora oryzae, Ophiostoma ulmi, Pectobacterium carotovorum, Pellicularia sasakii (Rhizoctonia solani), Peronospora manshurica, Phakopsora pachyrhizi, Phoma foveata, Phoma medicaginis, Phomopsis longicolla, Phytophthora cinnamomi, Phytophthora erythroseptica, Phytophthora fragariae, Phytophthora infestans, Phytophthora medicaginis, Phytophthora megasperma, Phytophthora palmivora, Podosphaera leucotricha, Pseudopeziza medicaginis, Puccinia graminis* subsp. *Tritici* (UG99), *Puccinia sorghi, Pyricularia grisea, Pyricularia oryzae, Pythium ultimum, Rhizoctonia solani, Rhizoctonia zeae, Rosellinia* sp., *Sclerotinia sclerotiorum, Sclerotinina trifoliorum, Sclerotium rolfsii, Septoria glycines, Septoria lycopersici, Setomelanomma turcica, Sphaerotheca macularis, Spongospora subterranea, Stemphylium* sp, *Synchytrium endobioticum, Thecaphora (Angiosorus), Thielaviopsis, Tilletia indica, Trichoderma viride, Ustilago maydis, Verticillium albo-atrum, Verticillium dahliae, Verticillium dahliae, Xanthomonas axonopodis, Xanthomonas oryzae* pv. *oryzae*.

In a preferred embodiment of the present invention, the application of the volatile compound composition to the plant results in a reduced occurrence of at least one plant disease caused by a bacterium, fungus, or insect as compared with plants not treated with the composition. In some embodiments, the plant disease is caused by *Aspergillus fumigatus, Botrytis cinerea, Cerpospora betae, Curvularia* spp., *Ganoderma boninense, Geotrichum candidum, Mycosphaerella fijiensis, Phytophthora palmivora, Phytophthora ramorum, Pythium ultimum, Rhizoctonia solani, Rhizopus* spp., *Schizophyllum* spp., *Sclerotinia sclerotiorum, Verticillium dahliae*, or *Xanthomonas axonopodis*. In a particularly preferred embodiment of the invention, the host plant is susceptible to diseases caused by *Ganoderma boninense*. In another preferred embodiment, the host plant is an oil palm plant. In other preferred embodiments, the disclosed compositions and methods are effective to kill the plant pathogen.

It is understood that all plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

As discussed above, the compositions and methods according to the present invention in principle can be applied to any plant. Therefore, monocotyledonous as well as dicotyledonous plant species are particularly suitable. The process is preferably used with plants that are important or interesting for agriculture, horticulture, for the production of biomass used in producing liquid fuel molecules and other chemicals, and/or forestry.

Thus, the invention has use over a broad range of plants, preferably higher plants pertaining to the classes of Angiospermae and Gymnospermae. Plants of the subclasses of the Dicotyledonae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Raffiesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

The methods of the present invention are preferably used in plants that are important or interesting for agriculture, horticulture, biomass for the production of biofuel molecules and other chemicals, and/or forestry. Non-limiting examples include, for instance, *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Arundo donax* (giant reed), *Secale cereale* (rye), *Salix* spp. (willow), *Eucalyptus* spp. (eucalyptus), *Triticosecale* spp. (triticum—wheat X rye), *Bamboo, Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum* usitatissimum (flax), *Brassica juncea, Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientate, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentine, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (petunia), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), *Phleum pratense* (timothy), and conifers. Of interest are plants grown for energy production, so called energy crops, such as cellulose-based energy crops like *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* spp. (triticum—wheat X rye), and *Bamboo*; and starch-based energy crops like *Zea mays* (corn) and *Manihot esculenta* (cassaya); and sucrose-based energy crops like *Saccharum* sp. (sugarcane) and *Beta vulgaris* (sugarbeet); and biofuel-producing energy crops like *Glycine max* (soybean), *Brassica napus* (canola), *Helianthus annuus* (sunflower), *Carthamus tinctorius* (safflower), *Jatropha curcas* (Jatropha), *Ricinus communis* (castor), *Elaeis guineensis* (African oil palm), *Elaeis oleifera* (American oil palm), *Cocos nucifera* (coconut), *Camelina sativa* (wild flax), *Pongamia pinnata* (Pongam), *Olea europaea* (olive), *Linum usitatissimum* (flax), *Crambe abyssinica* (Abyssinian-kale), and *Brassica juncea.*

Treatment of Soil with Volatile Organic Compounds

The invention provides for a method to treat soil or other similar plant growth media with compositions of the present invention. The invention provides a method to use compositions as disclosed herein to kill plant pathogens in soil. Typically, the composition comprises two or more volatile organic compounds and, optionally, an agricultural carrier. Carriers in some embodiments reduce loss of the volatile organic compounds during application. In some embodiments, the carriers are absorbent materials that can be soaked in or permeated with the composition, such that the absorbent material can hold and prevent immediate volatilization and diffusion of the compounds of the composition. Once mixed with the soil, the carrier can allow more gradual release of the volatile compounds through the soil. Examples of such carriers include, without limitation, peat, humus, vermiculite, shredded paper, paper, fabric, or wood fibers from waste or recycling processes, sawdust, ground of pulverized sugar bagasse, grain husks, or empty fruit bunches, etc. Other agricultural carriers include seeds, branches, mulch, plant fragments, and powdered milk. One agricultural carrier is soil itself. The soil or plant growth media may be treated prior to (e.g., a sterilization treatment before planting) or concurrent with plant growth (e.g., a treatment while planting, or after growth is established).

The volatile organic compounds are added to the soil. Mixing may then be performed to distribute the compounds throughout the vicinity of the target plant pathogen. In other embodiments, the volatile compound composition is mixed directly with the soil in the absence of a solid or particulate carrier.

In yet other embodiments; the composition is injected into the soil. For example, a composition that includes isobutyric acid, methyl isobutyrate, or butyric anhydride can be provided in a vessel under pressure, and can be injected about one, two, three, four, five, six, seven, eight, nine, ten, between ten and fifteen, or between fifteen and twenty centimeters, between twenty and thirty centimeters, between thirty and fifty centimeters, or further below the surface of the soil at intervals throughout an area that is planted with a plant species of interest, or will be planted with a plant species of interest. In some embodiments, the soil is covered after injection of the composition to reduce loss of the volatile compound. For example, plastic sheeting can be used to cover the injected area so that it remains covered for from about eight hours to about one month after injection.

The treated soil may be then used for planting of plants susceptible to pathogens that can be effectively inhibited or killed by the volatile organic compounds. In some embodiments, soil or plant growth medium is treated where plants have already been planted or established in the soil or growth medium. Volatile organic compounds may also be topically administered to plants, including all plant parts, specifically on, in, or near the roots of the oil palm. In some embodiments, soil may be treated while plants are growing in the soil.

In yet other embodiments, a compound of the invention is watered into the soil from an irrigation system, for example, a spray or drip irrigation system.

The composition with soil or an agricultural carrier may also be applied to the base of oil palm plants. The composition may also be directly applied to the roots of the plants. The plants may have root disease caused by a plant pathogen. The plant pathogen may be *Ganoderma boninense*. Other exemplary plant pathogens causing root diseases include *Phytophthora palmivora, Pythium ultimum*, or *Sclerotinia sclerotiorum*. It is desired that the volatile organic compounds inhibit growth of or kill plant pathogenic fungi such as *Ganoderma boninense, Phytophthora palmivora, Pythium ultimum*, and *Sclerotinia sclerotiorum.*

Another aspect of the invention provides a method for screening microbial strains that may be useful for treating, inhibiting or preventing the development of a plant pathogenic disease. The method involves (i) exposing or contacting candidate microbial strains with the invention composition, (ii) selecting microbial strains resistant to the composition, and (iii) characterizing the selected microbial strain. The characterization of the selected microbial strains can be carried by a variety of known molecular and microscopy techniques. Non-limiting examples of such techniques include electron microscopy, GC-MS analysis of VOC profile, PCR amplification and phylogenetic analysis of the 18S or the ITS-5.8S rDNA sequences.

The discussion of the general methods given herein is intended for illustrative purposes only. Other alternative methods and embodiments will be apparent to those skilled in the art upon review of this disclosure. The following examples are offered to illustrate, but not limit, the invention.

Example 1

Quantitative Analysis of Volatile Organic Compounds (Vocs) from *Muscodor strobelii*

The gases in the air space above a 14 day old culture of the MB-8 *Muscodor strobelii* growing on a Petri plate (PDA) were quantitatively analyzed (live culture deposited on Jun. 5, 2009 in the Agricultural Research Culture Collection located at 1815 N. University Street, Peoria, Ill. 61604, USA (NRRL) in accordance with the Budapest Treaty on the International Recognition of the Deposit of Microorganisms for the Purpose of patent Procedure and the Regulations thereunder (Budapest Treaty) as Accession Number NRRL 50288). First, a baked "Solid Phase Micro Extraction" syringe (Supelco) consisting of 50/30 divinylbenzene/carburen on polydimethylsiloxane on a stable flex fiber was placed through a small hole drilled in the side of the Petri plate sporting the growth of MB8. The fiber was exposed to the vapor phase of the fungus for 45 minutes. The syringe was then inserted into the splitless injection port of a Hewlett Packard 6890 gas chromatograph containing a 30 m×0.25 mm I.D. ZB Wax capillary column with a film thickness of 0.50 mm. The column was temperature programmed as follows: 30° C. for 2 minutes followed to 220° C. at 5° C./minute. The carrier gas was ultra high purity Helium (local distributor), and the initial column head pressure was 50 kPa. Prior to trapping the volatiles, the fiber was conditioned at 240° C. for 20 minutes under a flow of helium gas. A 30 second injection time was used to introduce the sample fiber into the GC. The gas chromatograph was interfaced to a Hewlett Packard 5973 mass selective detector (mass spectrometer) operating at unit resolution. Data acquisition and data processing were performed on the Hewlett Packard ChemStation software system. Initial identification of the unknowns produced by MB8 was made through library comparison using the NIST database. The identified compounds and their peak areas are provided in Table 2.

TABLE 2

VOCs Produced by a 14 Day Old Culture of *Muscodor strobelii* on PDA.

| Retention Time | Peak Area | Possible Compound | MW |
| --- | --- | --- | --- |
| 3.853 | 6.07 | Acetone | 58 |
| 4.287 | 2.28 | 2-Butanone | 72 |
| 4.887 | 33.13 | Isobutyric acid, methyl ester | 102 |
| 5.682 | 122.88 | Isobutyric acid | 88 |
| 5.740 | 3.77 | Methyl 2-methoxypropenoate | 116 |
| 5.903 | 2.29 | Acetic acid, (tert-butylthio)- | 148 |
| 6.389 | 2.86 | 2-Methylheptanoic acid | 144 |
| 6.504 | 0.35 | Methyl 2,3-dimethylbutanoate | 130 |
| 6.961 | 11.04 | Allyl 2-methylpropanoate (isobutyric anhydride) | 128 |
| 7.512 | 1.13 | N,2-dimethylpropanamide | 101 |
| 9.090 | 0.39 | Heptyl allyl oxalate | 228 |
| 9.931 | 0.26 | Butyl propyl oxalate | 188 |

TABLE 2-continued

VOCs Produced by a 14 Day Old Culture of *Muscodor strobelii* on PDA.

| Retention Time | Peak Area | Possible Compound | MW |
| --- | --- | --- | --- |
| 10.012 | 0.22 | 1-(ethenyloxy)-3-methyl-butane | 114 |
| 11.278 | 2.94 | alpha-Gurjunene | 204 |
| 11.332 | 2.15 | (−)-Aristolene | 204 |
| 11.436 | 1.07 | alpha-Patchoulene | 204 |
| 11.557 | 6.28 | 4,5-dimethyl-1,2,3,6,7,8,8a,8b-octahydrobiphenylene | 188 |
| 11.740 | 14.91 | (−)-tricyclo[6.2.1.0(4,11)]undec-5-ene,1,5,9,9-tetramethyl-(isocaryophyllene-II) | 204 |
| 11.929 | 0.44 | pentamethyl-benzene | 148 |
| 12.032 | 0.74 | Bergamotene | 204 |
| 12.099 | 0.14 | 4,4-diethyl-2,5-octadiyne | 162 |
| 12.190 | 0.34 | 2-(1-Propenyl)-6-methylphenol | 148 |
| 12.446 | 0.06 | (Z)-7,11-dimethyl-3-methylene-1,6,10-dodecatriene | 204 |
| 12.683 | 0.86 | 4,5-dehydro-isolongifolene | 202 |

Example 2

Use of Compositions of Volatile Organic Compounds to Kill Plant Pathogens

A composition containing a mixture of volatile compounds was prepared as follows: 47.5% isobutyric acid, 47.5% methyl ester of isobutyric acid (methyl isobutyrate), and 5% naphthalene.

To test the bioactivity, the mixture was placed in a small cup in the center of a Petri plate with potato dextrose agar (PDA) (Strobel et al., 2001 *Microbiology* 147: 2943-2950). The volumes of liquid tested were 0, 2.5, 5.0, 10.0 and 20 microliters as per Strobel et al., supra. Then small cubes of fungal inoculum grown on PDA were also applied to the plate. The plates were sealed with parafilm and incubated for 3 days, at which time measurements of hyphal development were made. Also, after 3 days the small plug of fungal inoculum was removed from the plate and transferred to a fresh PDA plate to determine if the test fungus was still alive (capable of growth) and this was recorded. The results showed that *Ganoderma boninense* and *Pythium ultimum* and *Phytophthora palmivora* were each killed by the lethal mixture of volatile compounds.

In another experiment, a composition containing a mixture of volatile compounds that included caryophyllene was tested for its ability to inhibit the growth of fungal pathogens. Caryophyllene is a sesquiterpene VOC that is found in products of certain plants, for example, essential oils such as clove oil. Additional examples of plant essential oils that can be present in a composition of the invention are provided in Table 3.

TABLE 3

Exemplary Plant Essential Oils basil oil
black pepper oil
(±)-camphor
carvacrol
trans-cinnamaldehyde
cinnamon leaf oil
cinnamon bark oil
citronellol
citral
(±)-citronellal

TABLE 3-continued

Exemplary Plant Essential Oils clove bud oil
eucalyptol
*eucalyptus* oil
eugenol
fennel oil
geraniol
ginger oil
jojoba oil
lemongrass oil
limonene
linalool
patchouli oil
peppermint oil
α-terpinene
rosemary oil
tea tree oil
thyme oil A mixture of 47.5% isobutyric acid; 47.5% isobutyric anhydride; and 5% caryophyllene was placed in a small cup in the center of a Petri plate with potato dextrose agar (PDA) and tested for activity on fungal as described above. The results showed that *Ganoderma boninense* and *Pythium ultimum* and *Phytophthora palmivora* were also each killed by this mixture of volatile compounds.

To determine the effectiveness of individual components of the tested VOC mixtures in killing pathogenic fungi, isobutyric acid and methyl isobutyrate were also tested on their own. In one experiment, isobutyric acid was placed in a small cup in the center of a Petri plate with potato dextrose agar (PDA) and tested for activity on fungi as described above. The results showed that the growth of each of *Ganoderma boninense* and *Pythium ultimum* and *Phytophthora palmivora* was inhibited by isobutyric acid alone, but not killed even at the higher concentrations.

In another experiment, the methyl ester of isobutyric acid (methyl isobutyrate) was placed in a small cup in the center of a Petri plate with potato dextrose agar (PDA) and tested for activity on fungi as described above. The results showed no growth inhibition of *Ganoderma boninense* and *Pythium ultimum* or *Phytophthora palmivora* occurred with methyl isobutyrate alone, even at the higher concentrations.

Example 3

Use of Compositions of Volatile Organic Compounds to Kill *Ganoderma boninense* in Soil Since the composition of Example 2 effectively killed *Ganoderma boninense*, 50 μl of the test mixture of Example 2 (47.5% isobutyric acid, 47.5% methyl ester of isobutyric acid (methyl isobutyrate), and 5% naphthalene) was applied to the base of a 5 ml sterile plastic tube containing autoclaved Malaysian sandy loam (from an oil palm plantation). The loam mixture had been inoculated with diced agar blocks containing a fresh culture of *Ganoderma boninense* which was equivalent to 0.5 mg dry weight of fungus mycelium. A control tube containing no artificial mixture was also set up. Both were incubated for three days and then plated on PDA. There was no fungal growth on the treated soil (plate on the right in FIG. 1), but on the control there was enormous growth of *Ganoderma boninense* (plate on the left in FIG. 1). The conclusion was that the VOC mixture had completely and effectively killed all hyphae of *Ganoderma boninense* that had been placed in the soil.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention and claimed herein. Headings within the application are solely for the convenience of the reader, and do not limit any way the scope of the invention or its embodiments.

All publications and patent applications mentioned in this specification are herein incorporated by reference to the same extent as if each individual publication or patent application was specifically can individually indicated to be incorporated by reference.

What is claimed is:

1. A method for treating, inhibiting or reducing the incidence of the development of a plant pathogenic disease, wherein said method comprises applying a composition in the vicinity of a host plant, said composition comprising:
   three or more compounds, wherein the first of said three or more compounds is isobutyric anhydride; and
   the second of said three or more compounds is selected from the group consisting of one or more of isobutyric acid, methyl isobutyrate, ethyl isobutyrate, propyl isobutyrate, isobutyric acid-allyl ester, and naphthalene, and
   the third of said three or more compounds is selected from the group consisting of one or more of: caryophyllene and a plant essential oil.

2. A method according to claim 1, wherein the second of said three or more compounds is isobutyric acid.

3. A method according to claim 2, wherein the third of said three or more compounds is caryophyllene.

4. A method according to claim 2, wherein the composition comprises 20-70% isobutyric anhydride and 20-70% isobutyric acid.

5. A method according to claim 1, wherein the composition comprises 1-10% naphthalene, or 1-10% caryophyllene, or 1-10% of a plant essential oil.

6. A method according to claim 4, wherein the composition further comprises 1-10% caryophyllene.

7. A method according to claim 1, wherein the composition further comprises an agriculturally effective amount of a pesticidal compound or composition selected from the group consisting of an acaricide, a bactericide, a fungicide, an insecticide, a microbicide, a nematicide, and a food preservative.

8. A method according to claim 1, wherein the composition is in the form of a powder, a granule, a pellet, a gel, an aqueous suspension, a solution, or an emulsion.

9. A method according to claim 1, wherein the composition further comprises an agriculturally acceptable carrier.

10. A method according to claim 9, wherein the carrier is a seed.

11. A method according to claim 1 wherein the host plant is a crop plant.

12. A method according to claim 1, wherein the host plant is an oil palm plant.

13. A method according to claim 1, wherein the second of said two or more compounds is selected from the group consisting of isobutyric acid, methyl isobutyrate, ethyl isobutyrate, propyl isobutyrate, and isobutyric acid-allyl ester.

14. A method according to claim 1, wherein said plant essential oil is selected from the group consisting of the plant essential oils listed in Table 3.

15. A method according to claim 4, wherein the composition comprises 42-53% isobutyric anhydride and 42-53% isobutyric acid.

16. A method according to claim 15, wherein the composition further comprises 3-7% caryophyllene.

17. A method according to claim 1 wherein the plant essential oil is isocaryophyllene or α-humulene.

18. A method according to claim 1 wherein the composition is applied or coated on a seed.

19. A method according to claim 1, wherein the pathogen is selected from the group consisting of *Aspergillus fumigatus, Botrytis cinerea, Cerpospora betae, Curvularia* sp., *Ganoderma boninense, Geotrichum candidum, Mycosphaerella fijiensis, Phytophthora palmivora, Phytophthora ramorum, Pythium ultimum, Rhizoctonia solani, Rhizopus* sp., *Schizophyllum* sp., *Sclerotinia sclerotiorum, Verticillium dahliae,* and *Xanthomona axonopodis.*

20. A method according to claim 1, wherein the composition is applied in the vicinity of or onto the roots, stems, trunk, seed, or leaves of the host plant.

21. A method according to claim 1, wherein the composition is injected into the roots, stems, trunk, seed, or leaves of the host plant.

22. A method for treating, inhibiting, or reducing the incidence of a plant pathogenic disease, said method comprising exposing or contacting the growth medium of a host plant to or with the composition of claim 1 prior to or concurrent with plant growth in said growth medium.

* * * * *